United States Patent
Stefan et al.

(10) Patent No.: US 9,782,188 B2
(45) Date of Patent: *Oct. 10, 2017

(54) MEDICAL INSTRUMENT

(71) Applicant: Karl Storz GmbH & Co. KG, Tuttlingen (DE)

(72) Inventors: Jochen Stefan, Wald (DE); Daniel Kaercher, Radolfzell (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 149 days.

This patent is subject to a terminal disclaimer.

(21) Appl. No.: 14/085,306

(22) Filed: Nov. 20, 2013

(65) Prior Publication Data

US 2014/0155933 A1    Jun. 5, 2014

(30) Foreign Application Priority Data

Nov. 20, 2012   (DE) .................. 10 2012 022 573

(51) Int. Cl.
| | | |
|---|---|---|
| *A61B 17/00* | (2006.01) | |
| *A61B 17/29* | (2006.01) | |
| *F16C 11/04* | (2006.01) | |

(52) U.S. Cl.
CPC ........ *A61B 17/29* (2013.01); *A61B 17/00234* (2013.01); *A61B 17/2909* (2013.01); *F16C 11/04* (2013.01); *A61B 2017/00464* (2013.01); *A61B 2017/00477* (2013.01); *A61B 2017/292* (2013.01); *Y10T 403/32114* (2015.01)

(58) Field of Classification Search
CPC ... A61B 17/00234; A61B 17/04; A61B 17/28; A61B 17/29; A61B 17/2909; A61B 2017/00464; A61B 2017/00477; A61B 2017/292
See application file for complete search history.

(56) References Cited

U.S. PATENT DOCUMENTS

| | | | | |
|---|---|---|---|---|
| 5,676,678 A * | 10/1997 | Schad | ............... | A61B 17/29 606/170 |
| 5,810,879 A | 9/1998 | de Guillebon | | |
| 6,077,290 A * | 6/2000 | Marini | ............... | A61B 17/29 600/564 |
| 6,322,579 B1 * | 11/2001 | Muller | ............... | A61B 17/1608 600/564 |
| 7,871,423 B2 * | 1/2011 | Livneh | ............... | A61B 17/1608 606/205 |

(Continued)

FOREIGN PATENT DOCUMENTS

| | | |
|---|---|---|
| AU | 2007221906 B1 | 10/2008 |
| DE | 19505032 A1 | 8/1995 |

(Continued)

*Primary Examiner* — Melanie Tyson
(74) *Attorney, Agent, or Firm* — Whitmyer IP Group LLC (57) ABSTRACT

A transmission adapter for a medical instrument with a shaft, a transmission device movable in the shaft, and a manipulating device with a first part, which can be coupled mechanically rigidly to a proximal end of the shaft, and a second part, which is movable relative to the first part, includes a first coupling element for releasable mechanical coupling to the second part of the manipulating device, and a second coupling element for releasable mechanical coupling to a proximal end of the transmission device.

3 Claims, 7 Drawing Sheets

(56) References Cited

U.S. PATENT DOCUMENTS

| | | | | |
|---|---|---|---|---|
| 8,876,805 | B2* | 11/2014 | Kaercher | A61B 17/00234 294/106 |
| 9,017,369 | B2* | 4/2015 | Renger | A61B 17/29 606/108 |
| 2004/0193212 | A1* | 9/2004 | Taniguchi | A61B 17/29 606/205 |
| 2008/0004656 | A1* | 1/2008 | Livneh | A61B 17/29 606/205 |

FOREIGN PATENT DOCUMENTS

| | | |
|---|---|---|
| DE | 102004025041 A1 | 12/2005 |
| DE | 102006038515 A1 | 2/2008 |
| DE | 102007021658 A1 | 11/2008 |
| DE | 102012200073 A1 | 7/2013 |
| EP | 1987790 A2 | 11/2008 |
| EP | 2510888 A1 | 10/2012 |
| EP | 2612609 A2 | 7/2013 |

* cited by examiner

MEDICAL INSTRUMENT

FIELD OF THE INVENTION

The present invention relates to a medical instrument with a shaft, a manipulating device at the proximal end of the shaft, and a transmission device movable in the shaft. In particular, the present invention relates to a possibility of a manipulating device being able to be combined with transmission devices of different designs.

BACKGROUND OF THE INVENTION

The regulations on the cleaning and sterilization of reusable medical instruments, in particular surgical instruments, place stringent demands requiring that the surgical instrument be able to be dismantled. In particular, the shaft and the manipulating device can generally be separated from each other. The manipulating device generally has at least two grip parts that are movable relative to each other, of which one is coupled to the shaft, and the other to a transmission rod arranged in the shaft. A movement of the two grip parts relative to each other results in a movement of the transmission rod in the shaft.

The proximal end of the transmission rod is designed in particular as a coupling element for releasable mechanical coupling to a grip part of the manipulating device. With different shaft diameters, transmission rods with different cross sections are used. Particularly if the transmission rod is connected to a tool separable from the shaft and can therefore be pulled out of the shaft in the distal direction, the size of the coupling element at the proximal end of the transmission rod depends on the cross section of the shaft.

In medical instruments for microinvasive interventions, there is a trend toward ever thinner shafts. This requires ever smaller coupling elements at the proximal ends of the transmission rods. Manipulating devices conventionally used with the same design for many different medical instruments can therefore no longer be used unchanged. Instead, the manipulating devices have to be modified and, in the worst case scenario, have to be adapted again and again to ever smaller coupling elements at proximal ends of transmission rods.

SUMMARY OF THE INVENTION

An object of the present invention is to create an improved medical instrument and to allow different shafts and different transmission devices to be combined with one and the same manipulating device, in particular with a conventional manipulating device.

This object is achieved by the subjects of the independent claims.

Developments are set forth in the dependent claims.

Illustrative embodiments of the present invention are based on the concept of providing a transmission adapter which can be coupled, on the one hand, to the proximal end of a transmission device in a shaft for a medical instrument and, on the other hand, to a manipulating device for a medical instrument. In particular, one transmission adapter is provided in each case for a plurality of different transmission devices, or for a plurality of transmission devices with differently designed coupling elements at their proximal ends. A distal end of the transmission adapter, or a coupling at the distal end of the transmission adapter, is in each case adapted to a defined shape of the proximal end of a transmission device, while the proximal ends of the transmission adapters are identical and in particular are adapted to a standard manipulating device.

A transmission adapter for a medical instrument with a shaft, a transmission device movable in the shaft, and a manipulating device with a first part, which can be coupled mechanically rigidly to a proximal end of the shaft, and a second part, which is movable relative to the first part, comprises a first coupling element for releasable mechanical coupling to the second part of the manipulating device, and a second coupling element for releasable mechanical coupling to a proximal end of the transmission device.

The transmission adapter is in particular a component part of a medical instrument or is provided and designed together with other component parts to form a medical instrument. The shaft is straight or curved, partially or completely rigid, or partially or completely elastically or plastically deformable. The transmission device is movable in translation and/or rotation in the shaft, in order to transmit a pulling and/or pushing force and/or a torque between the manipulating device and a distal end of the shaft, in particular a tool at the distal end of the shaft.

The first part and the second part of the manipulating device are in particular designed like the grip parts of a pair of scissors and can be moved relative to each other using the fingers of one hand. Alternatively, the first part and the second part of the manipulating device are designed like the grip parts of forceps. Alternatively, the manipulating device has a third part, which in particular is designed and arranged symmetrically with respect to the second part of the manipulating device, wherein the second part and the third part of the manipulating device are designed for releasable and joint mechanical coupling to the first coupling element of the transmission adapter. This design of the manipulating device can resemble the type of construction known from needle holders.

The manipulating device and in particular the first part thereof are designed, for example, for a releasable latched connection to the proximal end of a shaft. The second part of the manipulating device is connected in particular by a hinge (for example shaft or solid hinge) to the first part and is pivotable relative to the latter about a pivot axis perpendicular to the longitudinal axis of a shaft that is to be connected to the manipulating device.

The first coupling element is in particular arranged at the proximal end of the transmission adapter and is designed for a hinged mechanical coupling to the second part of the manipulating device. The second coupling element is in particular arranged at the distal end of the transmission adapter. Like the transmission device, the transmission adapter is also designed to transmit a force and/or a torque from the second part of the manipulating device to the proximal end of the transmission device.

The second coupling element of the transmission adapter can be designed for form-fit coupling to a proximal end of any desired transmission device. The transmission adapter can be adapted to any desired transmission device and to any desired manipulating device and can thus allow any desired transmission device to be combined with any desired manipulating device. In particular, ever thinner shafts and, accordingly, ever thinner transmission devices with ever smaller coupling elements at their proximal ends can be combined with a conventional manipulating device, in particular with a standard manipulating device. This dispenses with development costs, and with costs for new tools for the production of manipulating devices that are adapted to different transmission devices. As a result of a small variation between types and larger batch numbers, the production costs per item fall and there is less work involved in storage and logistics.

Moreover, the second coupling element of the transmission adapter is designed in particular for a releasable but rigid mechanical coupling to the proximal end of a transmission rod. A rigid coupling without a hinge dispenses with the wear and mechanical play which almost necessarily occur or exist in a hinged design. This can permit or simplify further miniaturization of transmission devices and of the proximal ends thereof. The first coupling element can be designed much larger than the proximal end of a transmission device and can thus be much less susceptible to wear and permit greater mechanical play.

In a transmission adapter as described here, the second coupling element in particular comprises a movable grip jaw for holding the proximal end of a transmission device with a form fit or force fit.

The second coupling element can comprise two or more movable grip jaws. In particular, the second coupling element comprises a stationary grip jaw and a movable grip jaw, or two grip jaws movable in opposite directions.

The movable grip jaw is in particular pivotable about a pivot axis.

The pivotability of the grip jaw is provided, for example, by a suitable bearing or a flexure hinge.

The movable grip jaw is in particular movable along a predetermined path.

In particular, guiding is provided by means of a slotted guide in the form of a slit, a groove or a web, wherein a slide surface defines the path. The grip jaw can be simultaneously pivotable about a pivot axis and movable along a predetermined path. In particular, the grip jaw is pivotable about a pivot axis, wherein an area of the grip jaw at a distance from the pivot axis is guided by means of the slotted guide.

One or more grip jaws can permit a robust and precise releasable mechanical coupling of the transmission adapter to a proximal end of given geometry of a transmission device, which mechanical coupling is easy to produce and at the same time reliable.

A transmission adapter with a movable grip jaw, as described here, also in particular comprises an elastic element, which is provided and designed to mechanically pretension the movable grip jaw to a position gripping the proximal end of the transmission device.

The elastic element is in particular coupled to the movable grip jaw in such a way that a deflection of the movable grip jaw from the gripping position causes a deformation of the elastic element, which results in a restoring force and/or a restoring torque, in order to move the movable grip jaw back to the gripping position. The elastic element can be designed in one piece with the movable grip jaw and/or with another part of the transmission adapter. The elastic element has in particular the shape of a leaf spring or of another spring. Alternatively, the elastic element can be designed in the form of an O-ring or of another body made from an elastomer or from another elastic material and, during a deflection of the movable grip jaw from the gripping position, can be stretched, compressed, sheared and/or twisted.

The elastic element can be designed to permit, without any further measures, a sufficiently strong mechanical coupling between the movable grip jaw and the proximal end of a transmission device. Alternatively, further measures may be provided in order to support or lock a mechanical coupling between the movable grip jaw and the proximal end of a transmission device.

In a transmission adapter as described here, the second coupling element in particular has a rotatable coupling member, wherein the rotatable coupling member is rotatable between a first position, in which a mechanical coupling to the proximal end of the transmission device can be produced and can be released, and a second position, in which a mechanical coupling to the proximal end of the transmission device is locked.

The rotatable coupling member is in particular rotatable about a rotation axis parallel to a longitudinal axis of the transmission device. The rotation axis of the rotatable coupling member is in particular spaced apart from the longitudinal axis of the transmission device. Alternatively, the coupling member can be rotatable about a rotation axis perpendicular to a longitudinal axis of the transmission device.

Independently of an arrangement of the rotation axis parallel or perpendicular to the longitudinal axis of a transmission device to be coupled to the coupling member, or in another orientation of the rotation axis, the rotatable coupling member in particular has a recess or an opening for receiving the proximal end of the transmission device. The opening on the rotatable coupling member has a first end and a second end. The first end of the opening is designed such that, in the first position of the rotatable coupling member, the proximal end of the transmission device can be received in the opening, at the first end of the opening, and can be removed therefrom. The second end of the opening is designed such that, in the second position of the rotatable coupling member, the proximal end of the transmission device is held in the opening, at the second end of the opening. In particular, the opening has, at the first end, a large width or a large cross section and, at the second end, a small width or a small cross section. An example is a keyhole-shaped configuration of the opening.

Alternatively, the second coupling element on the transmission adapter can be designed for a releasable mechanical coupling that can be produced or locked, and released or unlocked, by a relative rotation of transmission device and second coupling element about an axis parallel to the longitudinal axis of the transmission device.

Alternatively, the second coupling element on the transmission adapter can be designed as a latched connection to the proximal end of a transmission device. In particular, a spring-mounted latch is provided which is designed to engage in an opening, recess or undercut at the proximal end of a transmission device. The latched connection by means of the spring-mounted latch can be manually released by actuation of a push button or another means.

A transmission adapter, as described here, is in particular integrated in a proximal area of a shaft.

In particular, the transmission adapter is integrated in the portion of a shaft that is provided and designed for arrangement in a corresponding recess in a manipulating device. Therefore, the transmission adapter, or the space needed for it, does not require any enlargement of the cross section of the shaft. Moreover, contamination of the transmission adapter during use of the shaft is unlikely at the proximal end of the shaft. Cleaning the shaft with the transmission adapter is thus made easier.

In a transmission adapter as described here, the second coupling element is in particular designed to be locked when the transmission adapter is arranged in a manipulating device.

The second coupling element is in particular designed so as to be locked in the sense that it cannot be opened, or uncoupling is impossible, when the transmission adapter is arranged in the manipulating device. A mechanical coupling between the transmission adapter and the proximal end of a transmission device is therefore only possible as long as the transmission adapter is arranged outside a manipulating device. If a predetermined sequence is observed in dismantling or assembling the component parts of a medical instrument, the locking of the second coupling element permits a reliable mechanical coupling of the transmission adapter to the proximal end of a transmission device. In particular, a medical instrument with the transmission adapter can be designed such that, during dismantling and assembly, the same maneuvers are required in the same sequence as in the case of a conventional instrument, of which the tool is permanently connected to the distal end of the transmission device.

In a transmission adapter as described here, the proximal end of the transmission adapter has in particular a surface portion in the shape of a spherical surface.

In particular, the proximal end of the transmission adapter has substantially the shape of a ball. In this way, the transmission adapter can permit the combination of any desired transmission device with a standard manipulating device, for example, in the case of a diameter of 2.5 mm, with a manipulating device from the product range offered by the applicant under the name "Clickline".

In a transmission adapter as described here, the second coupling element is in particular designed to transmit a torque to a transmission device coupled to the second coupling element.

The second coupling element is in particular designed such that, by form fit with a correspondingly designed transmission device, it is able to transmit a torque to this transmission device. For this purpose, the second coupling element in particular has a shape that is not purely rotationally symmetrical with respect to the longitudinal axis of a transmission device to be coupled to the second coupling element. In particular, the second coupling element defines a cavity of polygonal (in particular rectangular) cross section, in order to receive a proximal end of a transmission device of corresponding cross section.

A design of the second coupling element of the transmission adapter such that a torque can be transmitted to a transmission device coupled to the second coupling element can, for example, permit a rotation of a tool at the distal end of a shaft, by corresponding rotation of the transmission adapter and of the transmission device. Moreover, the design of the second coupling element of the transmission adapter such that a torque can be transmitted to a transmission device coupled to the second coupling element can allow the transmission device to be held in a predetermined rotation position. In particular, a releasable mechanical coupling of a tool to a distal end of a shaft (for example by means of a bayonet coupling or screw coupling) can be locked, by means of the proximal end of the transmission device being held in a predetermined position (in respect of a rotation about the longitudinal axis of the transmission device) by the transmission adapter or by the second coupling element thereof.

A shaft for a medical instrument comprises a proximal end for coupling to a first part of a manipulating device, a distal end for coupling to a tool, and a transmission adapter, as described here, which is movable relative to the shaft.

In particular, the transmission adapter is arranged inside the shaft, and at the proximal end thereof, and is movable in translation and/or rotation relative to the shaft. The integration of the transmission adapter in a shaft, in particular in a proximal area of the shaft provided and designed for arrangement in a manipulating device, can permit completely unchanged use or handling in relation to conventional medical instruments. Since each shaft is generally designed for a transmission device of predetermined cross section, the transmission adapter in the shaft can be readily adapted to the proximal end of the transmission device.

The transmission adapter can be integrated in the shaft in such a way that it cannot be removed from the shaft, or cannot be removed from the latter without destruction or without the use of a tool, and therefore also cannot be lost, and it is protected in the shaft from mechanical damage.

In a shaft as described here, the second coupling element of the transmission adapter is designed to transmit a torque to a transmission device coupled to the second coupling element, in order to lock a releasable mechanical coupling of a tool to the distal end of the shaft.

The second coupling element is designed in particular in such a way that, by means of a form fit, it is able to transmit a torque to a transmission device coupled to the second coupling element. In particular, the second coupling element of the transmission adapter is designed to hold the transmission device in a predetermined position with respect to a rotation about its longitudinal axis, in which position the releasable mechanical coupling of a tool to the distal end of the shaft is locked. For this purpose, the transmission adapter is in particular guided in the shaft such that, although it is movable parallel to the longitudinal axis, it is not rotatable about the longitudinal axis. Thus, although axial or longitudinal forces and corresponding movements can be transmitted to the transmission device by means of the transmission adapter, a rotation of the transmission adapter and of the transmission device is blocked.

A shaft adapter comprises a proximal end for coupling to a first part of a manipulating device, a distal end for coupling to a proximal end of a shaft, and a transmission adapter, as described here, which is movable relative to the shaft adapter.

In particular, the transmission adapter is arranged inside the shaft adapter and is movable in translation and/or rotation relative to the shaft adapter. If the shaft adapter, in particular the distal end thereof, is designed for coupling to a proximal end of a predetermined shaft, or of a shaft of a predetermined type, the transmission adapter in the shaft adapter can be designed for coupling to a proximal end of a transmission device that is provided and designed for use with the predetermined shaft, or with a shaft of a predetermined type. The shaft adapter can permit a combination of a shaft (and therefore of a transmission device) and a manipulating device that are not conventionally designed for combination with each other.

A shaft or a shaft adapter with a transmission adapter having a movable grip jaw, as described here, further comprises in particular a lateral opening, wherein the movable grip jaw is arranged at least partially in the lateral opening, wherein the movable grip jaw is designed to lie completely within the contour of the shaft or of the shaft adapter when a proximal end of a transmission device is held with a form fit by the movable grip jaw, and to protrude beyond the contour of the shaft or of the shaft adapter when the transmission adapter is uncoupled from a proximal end of a transmission device.

The lateral opening is in particular arranged in a substantially cylindrical (in particular circularly cylindrical) area of the shaft or of the shaft adapter. The contour of the shaft is in particular the contour or the outer edge of the cross section of the shaft immediately proximal and/or immediately distal from the lateral opening. In particular, the shaft or the shaft adapter, in the area of the opening, is substantially (i.e. apart from the lateral opening) cylindrical or circularly cylindrical.

If the area of the shaft or of the shaft adapter comprising the lateral opening is arranged in a recess of corresponding shape in a manipulating device, the movable grip jaw is held, by the surface of the recess, in the position holding the proximal end of a transmission device with a form fit and is prevented from deflecting from this position. In this way, the mechanical coupling between the transmission adapter and the transmission device is locked. It is only when the shaft or shaft adapter is removed from the recess in the manipulating device that the movable grip jaw or the movable grip jaws can be deflected, from their position holding the proximal end of a transmission device with a form fit, to beyond the contour of the shaft or the shaft adapter, thereby allowing the mechanical coupling between transmission adapter and transmission device to be produced or released.

A medical instrument comprises a manipulating device with a first part, and a second part which is movable relative to the first part, a shaft with a proximal end, which can be coupled mechanically to the first part of the manipulating device, and a distal end, a transmission device, movable in the shaft, for transmitting at least either a force or a torque between the second part of the manipulating device and the distal end of the shaft, and a transmission adapter as described here.

A tool can be provided at the distal end of the shaft or can be coupled mechanically to the distal end of the shaft. The transmission device is in particular movable in translation and/or rotation in the shaft. The second part of the manipulating device is in particular pivotable with respect to the first part.

In a medical instrument as described here, the transmission adapter is in particular a component part of a shaft, as described here, or of a shaft adapter, as described here.

In a medical instrument as described here, the transmission device has, in an area provided for the mechanical coupling to the second coupling element of the transmission adapter, a cross section that is not rotationally symmetrical with respect to the longitudinal axis, wherein the second coupling element of the transmission adapter has a cross section that corresponds to the non-rotationally symmetrical cross section of the transmission device.

The cross section of the transmission device, not rotationally symmetrical with respect to the longitudinal axis of the transmission device, is in particular rectangular or substantially rectangular or of another polygonal shape. In particular, the transmission device has, in the area provided for the mechanical coupling to the second coupling element of the transmission adapter, a flattening with a cross section having one or two mutually opposite and substantially flat surfaces.

The corresponding non-rotationally symmetrical cross sections of the transmission device and of the second coupling element of the transmission adapter permit a form-fit coupling of the transmission device and of the transmission adapter and a form-fit transmission of a torque between the two.

In particular, the transmission adapter is guided in the shaft in such a way that, although it is movable parallel to the longitudinal axis, it is not rotatable about the longitudinal axis. Thus, although axial or longitudinal forces and corresponding movements can be transmitted to the transmission device by means of the transmission adapter, a rotation of the transmission adapter and of the transmission device is blocked. The form-fit connection between the transmission adapter and the transmission device allows the transmission device to be held in a predetermined position (with respect to a rotation about the longitudinal axis) and, therefore, for example, allows a releasable mechanical connection between a tool and the distal end of the shaft of the medical instrument to be locked.

A medical instrument, as described here, comprises in particular a plurality of alternatively usable transmission devices with differently designed proximal ends, and a plurality of alternatively usable transmission adapters, wherein the first coupling elements of all the transmission adapters are identical and designed for releasable mechanical coupling to the second part of the manipulating device, wherein the second coupling elements of the plurality of transmission adapters are designed differently, and wherein each transmission adapter has a second coupling element which is designed for releasable mechanical coupling to a proximal end of one of the transmission devices.

In particular, for each transmission device, there exists one transmission adapter, of which the second coupling element is designed for releasable mechanical coupling to the proximal end of the transmission device.

BRIEF DESCRIPTION OF THE FIGURES

Embodiments are explained in more detail below with reference to the attached figures, in which.

DETAILED DESCRIPTION OF THE INVENTION

Figure 1:
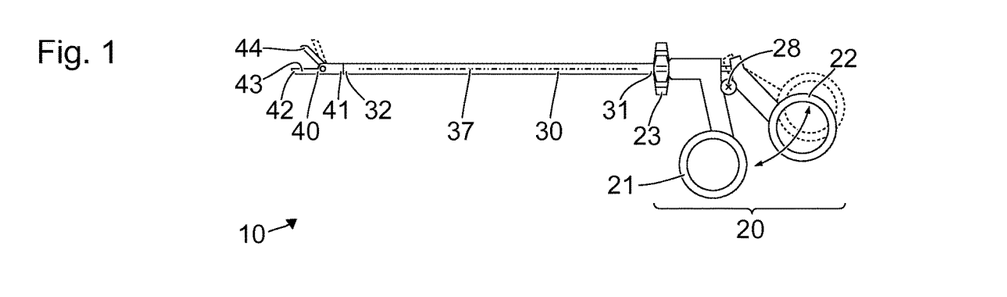
FIG. 1 shows a schematic view of a medical instrument.

FIG. 1 shows a schematic view of a medical instrument 10, in particular of an instrument for microinvasive surgery, with a manipulating device 20 at the proximal end, a shaft 30, and a tool 40.

The manipulating device comprises a first, stationary part 21, a second, movable part 22, and a wheel 23. The second part 22 is connected to the first part 21 by a hinge, in such a way that it is pivotable relative to the first part 21 about a pivot axis 28 perpendicular to the plane of the drawing in FIG. 1.

The shaft 30 comprises a proximal end 31, which is mechanically coupled to the manipulating device 20 in a releasable manner, and a distal end 32, which is mechanically coupled to the tool 40 in a releasable manner. The shaft 30 is rigid or flexible, straight or curved. In the example shown, the shaft 30 is straight and has a longitudinal axis 37, in relation to which the shaft 30 is rotationally symmetrical. The proximal end 31 of the shaft 30 is mechanically coupled to the wheel 23 in such a way that, by means of the wheel 23, it is possible for the shaft 30, and for the tool 40 at the distal end 32 of the shaft 30, to be rotated about the longitudinal axis 37 of the shaft 30.

The tool 40 has a proximal end 41, which is mechanically coupled to the distal end 32 of the shaft 30 in a releasable manner, and a distal end 42. At the distal end 42, the tool 40 has a stationary jaw part 43 and a pivotable jaw part 44. By way of a transmission rod (not shown in FIG. 1) movable in the shaft 30, the pivotable jaw part 44 is coupled to the second part 22 of the manipulating device 20 such that a movement of the second part 22 of the manipulating device 20 relative to the first part 21 causes a movement of the pivotable jaw part 44 relative to the stationary jaw part 43 about a pivot axis perpendicular to the plane of the drawing in FIG. 1. For this purpose, the transmission rod (not shown in FIG. 1) is movable particularly in translation inside the shaft 30, parallel to the longitudinal axis 37 of the shaft 30, in order to transmit a pulling or pushing force between the second part 22 of the manipulating device 20 and the pivotable jaw part 44 of the tool 40. Alternatively or in addition, the transmission rod can be rotatable in the shaft 30 (in particular about the longitudinal axis 37 of the shaft 30), in order to transmit a torque between the manipulating device 20 and the tool 40.

In FIG. 1, solid lines show the pivotable jaw part 44 of the tool 40 in an open position and the second part 22 of the manipulating device 20 in a corresponding position. Broken lines show the pivotable jaw part 44 of the tool 40 in a wider open position and the second part 22 of the manipulating device 20 in a corresponding position. When the second part 22 of the manipulating device 20 is pivoted in the direction of the first part 21 starting from the position shown in solid lines, the pivotable jaw part 44 of the tool 40 is pivoted toward the stationary jaw part 43 starting from the open position shown in solid lines.

Figure 2:
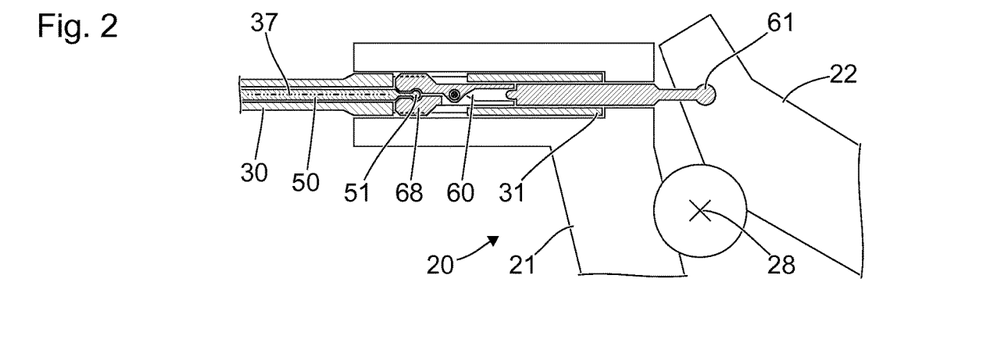
FIG. 2 shows a schematic view of a transmission adapter in a shaft.

FIG. 2 shows a schematic and enlarged view of a partial area of the medical instrument 10 from FIG. 1. It shows in particular a section through the proximal end 31 of the shaft 30 and a part of the manipulating device 20. The sectional plane contains the longitudinal axis 37 of the shaft 30. Sectional surfaces of the shaft 30, of a transmission rod or pulling rod or a transmission device 50, and of a transmission adapter 60 are shown by hatching. The parts 21, 22 of the manipulating device are only indicated in outline, in order to differentiate them more clearly from the shaft 30, transmission device 50 and transmission adapter 60. The wheel 23 indicated in FIG. 1, and devices for the rotary coupling of the wheel 23 to the shaft 30 or to the transmission device 50, are not shown in FIG. 2.

The proximal end 31 of the shaft 30 is arranged in a recess of corresponding shape in the first part 21 of the manipulating device 20. The shaft 30, or the proximal end 31 thereof, can be locked mechanically in a releasable manner in the manipulating device 20, or in the first part 21 thereof, for example by means of a spring-loaded detent (not shown in FIG. 2) which engages in a recess on the shaft 30.

Like a tube, the shaft 30 has a lumen in which the transmission device 50 is arranged. The lumen in the shaft 30 and the transmission device 50 each have substantially a circular cylindrical configuration. The cross section of the lumen in the shaft 30 and the cross section of the transmission device 50 are chosen such that the transmission device 50 is movable in the shaft 30 in a direction parallel to the longitudinal axis 37 of the shaft 30 and is rotatable about the longitudinal axis 37 and guided with minimal play and friction. A proximal end 51 of the transmission device 50 is substantially spherical.

The transmission adapter 60 is largely arranged inside the shaft 30, near the proximal end 31 of the latter. The transmission adapter 60 comprises a first coupling element 61 at its proximal end and a second coupling element 68 at its distal end. The first coupling element 61 has substantially the shape of a ball and is coupled in a hinged manner to the second part 22 of the manipulating device 20. In the position of the second part 22 of the manipulating device 20 as shown in FIG. 2, which corresponds to the wider open position of the pivotable jaw part 44 of the tool 40 described above with reference to FIG. 1, the mechanical coupling between the first coupling element 61 of the transmission adapter 60 and the second part 22 of the manipulating device 20 can be produced or released. The mechanical coupling between the first coupling element 61 of the transmission adapter 60 and the second part 22 of the manipulating device 20 corresponds in particular to a conventional mechanical coupling between the proximal end of a conventional transmission device and the pivotable part of a conventional manipulating device. Therefore, details of this mechanical coupling are not given here.

The second coupling element 68 at the distal end of the transmission adapter 60 is coupled mechanically to the proximal end 51 of the transmission device 50. Details are given below with reference to FIGS. 5 to 8.

Figure 3:
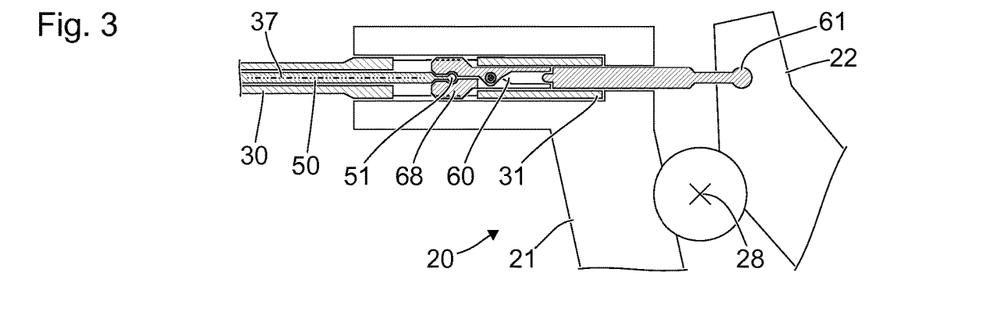
FIG. 3 shows another schematic view of the transmission adapter from FIG. 2.

The transmission device 50 and the transmission adapter 60 are movable parallel to the longitudinal axis 37 of the shaft 30. FIG. 3 shows another schematic view which, in terms of the features shown and of the sectional plane, corresponds to FIG. 2. However, compared to the view in FIG. 2, the transmission device 50 and the transmission adapter 60 in the view in FIG. 3 have been moved in the proximal direction. Accordingly, the second part 22 of the manipulating device 20 is pivoted (clockwise) about the pivot axis 28.

Between the proximal end 51 of the transmission device 50 and the second coupling element 68 of the transmission adapter 60, there is a mechanical connection which, although releasable, is rigid in the unreleased state (in particular free of play or with minimal play). Therefore, each movement of the first coupling element 61 and each force exerted on the first coupling element 61 of the transmission adapter 60 in a direction parallel to the longitudinal axis 37 of the shaft 30 is transmitted to the transmission device 50 and from this to the distal end of the medical instrument 10 and to the tool 40, and vice versa.

Figure 4:
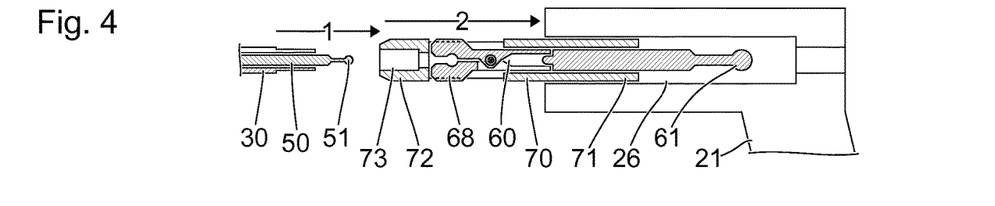
FIG. 4 shows a schematic view of a transmission adapter in a shaft adapter.

FIG. 4 shows a schematic view of a section through a shaft 30, a transmission device 50, a shaft adapter 70, and a transmission adapter 60 arranged in the shaft adapter 70. The nature of the view, in particular the sectional plane shown, corresponds substantially to that of FIGS. 2 and 3. For reasons of space, only a partial area of the first part 21 of the manipulating device is shown.

The illustrative embodiment in FIG. 4 differs from the illustrative embodiment in FIGS. 2 and 3 in that the transmission adapter 60 is not arranged in the proximal end 31 of the shaft 30, or in an area near the proximal end 31, but instead in a separate shaft adapter 70. The shaft adapter 70 has a proximal end 71 and a distal end 72 with a recess 73. The shaft adapter 70 is designed (like a proximal area of the shaft 30 in the illustrative embodiment in FIGS. 2 and 3) to be received in a recess 26 in the first part 21 of the manipulating device. The recess 73 at the distal end 72 of the shaft adapter 70 is designed to receive the proximal end of the shaft 30.

In FIG. 4, the shaft 30 with the transmission device 50 on the one hand, and the shaft adapter 70 with the transmission adapter 60 on the other hand, and also the first part 21 of the manipulating device, are each shown separately. An arrow labeled "1" indicates how the shaft 30 with the transmission device 50 can be inserted into the recess 73 at the distal end 72 of the shaft adapter 70, and the second coupling element 68 of the transmission adapter 60. An arrow labeled "2" indicates how the shaft adapter 70 with the transmission adapter 60, which in the view in FIG. 4 are shown only partially inserted in the recess 26 in the first part 21 of the manipulating device, can be inserted completely into said recess 26. It will be shown below that in particular the coupling of the proximal end 51 of the transmission device 50 to the second coupling element 68 of the transmission adapter 60 according to the arrow "1" has to take place before the complete insertion of the shaft adapter 70 with the transmission adapter 60 into the recess 26 in the first part 21 of the manipulating device.

FIGS. 5 to 8 show schematic and enlarged sectional views of a transmission adapter 60 which, in terms of many features, is similar to the transmission adapters described above with reference to FIGS. 2 to 4. The sectional planes of FIGS. 5 to 8 correspond to the sectional planes of FIGS. 2 to 4 and are parallel to the longitudinal axis 37 (cf. FIGS. 1 to 3) of the shaft 30. The views in FIGS. 5 to 8 differ from one another in terms of different positions and states of a transmission device 50 and of the transmission adapter 60.

In FIGS. 5 to 8, the transmission adapter 60 is in each case shown in a proximal area of a shaft 30 or in a shaft adapter 70. Since a shaft 30 and a shaft adapter 70 do not differ in terms of the features shown in FIGS. 5 to 8, but instead only differ at the distal end (cf. FIGS. 3 and 4), the following explanation with reference to FIGS. 5 to 8 applies both to a shaft and also to a shaft adapter.

The transmission adapter 60 comprises a main body 64 with an abutment 67, a first grip jaw 81 and a second grip jaw 82. The first grip jaw 81 and the second grip jaw 82 form the second coupling element 68 (cf. FIGS. 2 to 4) of the transmission adapter 60. The first grip jaw 81 and the second grip jaw 82 are connected in a hinged manner to the main body 64 of the transmission adapter 60 and are pivotable independently of each other about a pivot axis 88 perpendicular to the planes of the drawings in FIGS. 5 to 8. Details of the connection between main body 64 and grip jaws 81, 82, by way of spars not shown in FIGS. 5 to 8, are described below with reference to FIG. 13.

The shaft 30 and the shaft adapter 70 have two lateral openings 38 lying opposite each other. The grip jaws 81, 82 are arranged partially in the openings 38 and, in the positions shown in FIG. 5, lie completely within the contour of the shaft 30 or of the shaft adapter 70. Each grip jaw 81, 82 is designed in one piece with an associated elastic element 87. The elastic elements 87 are each beam-shaped. Ends of the elastic elements facing away from the grip jaws 81, 82 bear on the abutment 67 on the main body 64 of the transmission adapter 60 and are supported thereon. Forces or torques applied by the elastic elements 87 to the grip jaws 81, 82 keep the latter in the positions shown in FIG. 5, as long as no external force acts on them.

Figure 5:
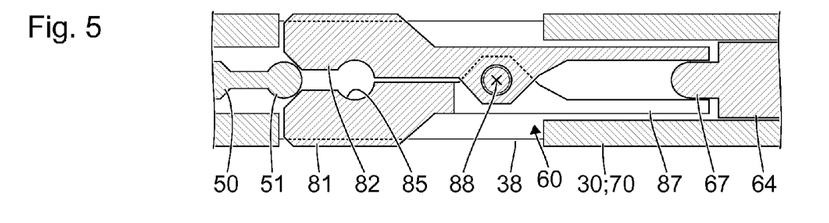
FIG. 5 shows a schematic view of a transmission adapter.
Figure 6:
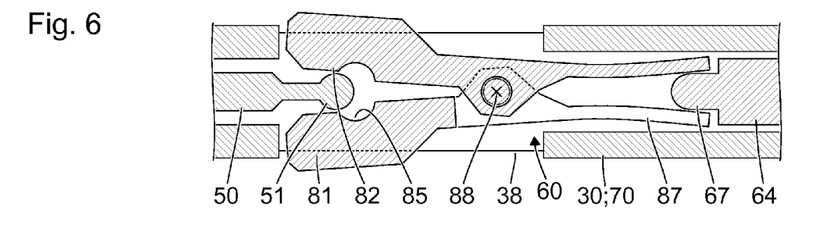
FIG. 6 shows another schematic view of the transmission adapter from FIG. 5.

When the proximal end 51 of the transmission device 50 is pushed in the proximal direction and thereby pressed against the grip jaws 81, 82 (in particular the oblique slide surfaces indicated), the grip jaws 81, 82 are deflected from the positions shown in FIG. 5 to the positions shown in FIG. 6. The grip jaws 81, 82 are pivoted in opposite directions about the pivot axis 88, and the elastic elements 87 are elastically deformed. The elastic deformation of the elastic elements 87 effects a restoring force or a restoring torque in the direction of the positions of the grip jaws 81, 82 shown in FIG. 5.

In the excursion of the grip jaws 81, 82 shown in FIG. 6, the outer areas (in FIG. 6 the lower area of the first grip jaw 81 and the upper area of the second grip jaw 82) protrude beyond the contour of the shaft 30 or of the shaft adapter 70.

If, starting from the position shown in FIG. 6, the transmission device 50 is pushed farther in the proximal direction, the proximal end 51 of the transmission device 50 reaches recesses 85 in the grip jaws 81, 82. The shape of the recesses 85 corresponds to the shape of the proximal end 51 of the transmission device 50. In particular, both the proximal end 51 of the transmission device 50 and also the recesses 85 are spherical. When the proximal end 51 of the transmission device 50 has reached its most proximal position relative to the transmission adapter 60, the grip jaws 81, 82 are moved by the elastic elements 87 into the positions shown in FIG. 7, which correspond completely or substantially to the positions shown in FIG. 5. The proximal end 51 of the transmission device 50 lies in the recesses 85 in the grip jaws 81, 82 and is thus held by these with a form fit.

When a sufficient pulling force is applied to the transmission device 50 in the distal direction, the proximal end 51 of the transmission device 50 can be released from the form-fit connection to the grip jaws 81, 82. The grip jaws 81, 82 are then brought (temporarily) to the positions shown in FIG. 6 counter to the forces or torques exerted by the elastic elements 87.

Figure 7:
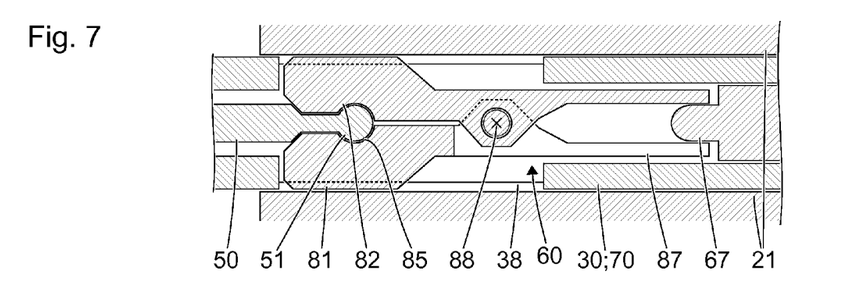
FIG. 7 shows another schematic view of the transmission adapter from FIGS. 5 and 6.
Figure 8:
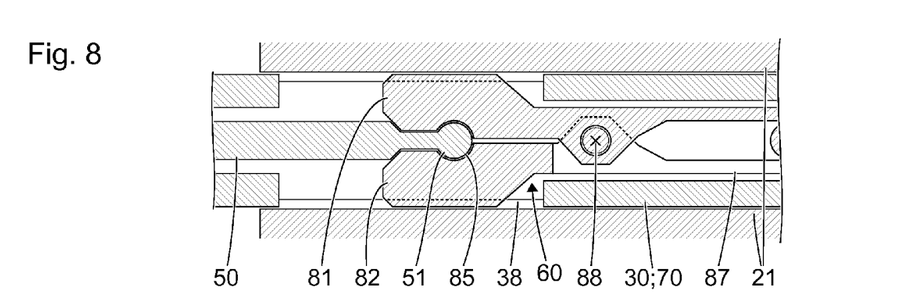
FIG. 8 shows another schematic view of the transmission adapter from FIGS. 5 to 7.

In the views in FIGS. 7 and 8, the illustrated proximal area of the shaft 30, or the shaft adapter 70, and the transmission adapter 60 are arranged in a recess in a part 21 of a manipulating device (cf. FIGS. 2 to 4). In FIGS. 7 and 8, only the immediately adjoining walls or areas of the part 21 of the manipulating device are indicated. The grip jaws 81, 82 bear on the part 21 of the manipulating device and are prevented by the latter from deflecting to the positions shown in FIG. 6. In this way, the mechanical coupling between the proximal end 51 of the transmission device 50 and the coupling element formed by the grip jaws 81, 82 at the distal end of the transmission adapter 60 is locked. The mechanical connection between the proximal end 51 of the transmission device 50 and the transmission adapter 60 can therefore be produced or separated only when the transmission adapter 60 is located, together with the shaft 30 or the shaft adapter 70, outside the part 21 of the manipulating device.

The lateral openings 38 in the proximal area of the shaft 30 or in the shaft adapter 70 are substantially longer, or have a length, measured in a direction parallel to the longitudinal axis 37 of the shaft 30 (cf. FIGS. 1 to 3), which is substantially greater than the areas of the grip jaws 81, 82 arranged in the lateral openings 38. Therefore, the grip jaws 81, 82 are movable in a direction parallel to the longitudinal axis of the shaft. In FIGS. 7 and 8, the transmission device 50 and the transmission adapter 60 are shown in different positions, which in particular correspond to different positions of the pivotable jaw part 44 (cf. FIG. 1) of a tool at the distal end of the medical instrument.

Figure 9:
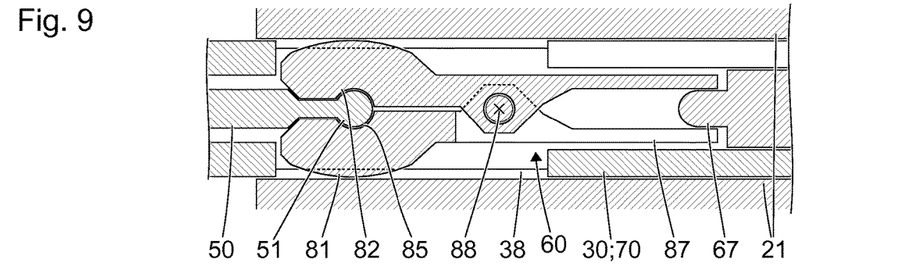
FIG. 9 shows a schematic view of another transmission adapter.

FIG. 9 shows a schematic view of another transmission adapter 60 which, in terms of some features, is similar to the transmission adapter described above with reference to FIGS. 5 to 8. The nature of the view, in particular the sectional plane shown, corresponds to the views in FIGS. 5 to 8.

The transmission adapter 60 shown in FIG. 9 differs from the transmission adapter described above with reference to FIGS. 5 to 8 particularly in that the outer surfaces of the grip jaws 81, 82 are convexly curved, in particular cylindrically (with a cylinder axis perpendicular to the plane of the drawing) or spherically.

Figure 10:
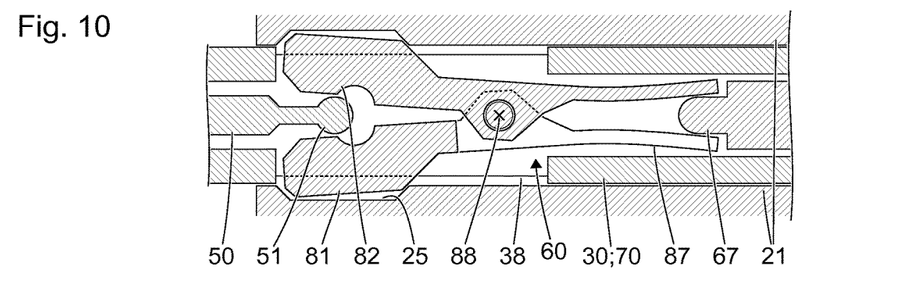
FIG. 10 shows a schematic view of another transmission adapter.

FIG. 10 shows a schematic view of another transmission adapter 60 which, in terms of some features, is similar to the transmission adapters 60 described above with reference to FIGS. 5 to 9. The nature of the view, in particular the sectional plane shown, corresponds to the views in FIGS. 5 to 9.

In contrast to the properties and features described above with reference to FIGS. 7 and 8, the transmission adapter 60 of FIG. 10 is arranged in a part 21 of a manipulating device that has recesses 25. The recesses 25 each have a shape corresponding to the outer areas of the grip jaws 81, 82. Therefore, the grip jaws 81, 82, in their most distal position as shown in FIG. 10, can be deflected to the positions also shown in FIG. 6, in which positions a mechanical connection to the proximal end 51 of a transmission device 50 can be produced or released. By contrast, when the transmission adapter 60 with the grip jaws 81, 82 is moved in the proximal direction (cf. FIG. 8), the mechanical coupling between the transmission device 50 and the transmission adapter 60 is locked, similarly to the manner described above with reference to FIGS. 7 and 8.

Figure 11:
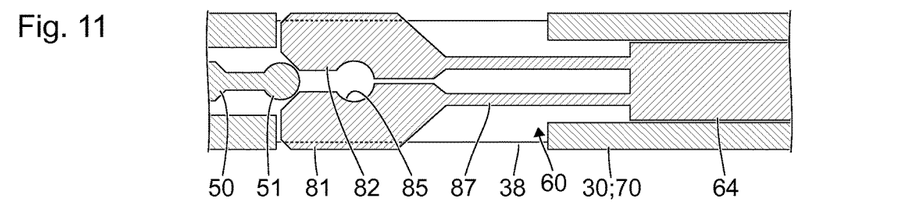
FIG. 11 shows a schematic view of another transmission adapter.

FIG. 11 shows a schematic view of another transmission adapter 60 which, in terms of some features, is similar to the transmission adapters 60 described above with reference to FIGS. 5 to 10. The view in FIG. 11 corresponds to the views in FIGS. 5 to 10, particularly as regards the sectional plane shown.

In the illustrative embodiment in FIG. 11, the elastic elements 87 are designed as solid hinges, which connect the main body 64 integrally to the grip jaws 81, 82. The elastic elements 87 thus fulfil two functions at the same time, namely the hinged connection to the main body 64 and the restoring action.

Figure 12:
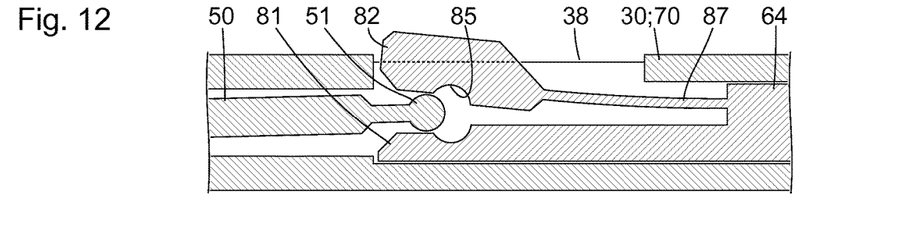
FIG. 12 shows a schematic view of another transmission adapter.

FIG. 12 shows a schematic view of another transmission adapter 60 which, in terms of some features, is similar to the transmission adapters 60 described above with reference to FIGS. 5 to 11. The view in FIG. 12 corresponds to the views in FIGS. 5 to 11, particularly as regards the sectional plane shown.

The illustrative embodiment in FIG. 12 differs from the illustrative embodiments described above with reference to FIGS. 5 to 11 particularly in that the first grip jaw 81 is connected rigidly to the main body 64 of the transmission adapter 60. Only the second grip jaw 82 is connected to the main body 64 in a hinged manner, specifically by an elastic element 87 designed as a flexure hinge in the example shown. When a mechanical connection between the transmission device 50 and the transmission adapter 60 is produced or released, only a deflection of the second grip jaw 82 takes place. Corresponding to this asymmetrical movement, a deflection of the transmission device 50, in particular of the proximal end 51 thereof, is needed, which can be seen in FIG. 12.

Figure 13:
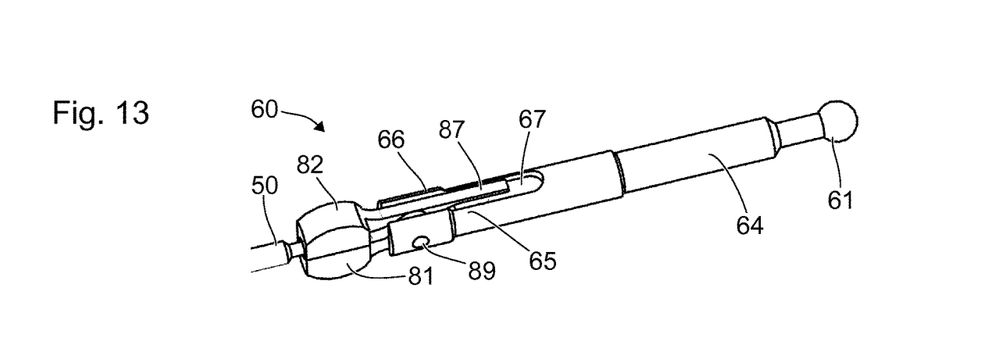
FIG. 13 shows a schematic view of another transmission adapter.
Figure 14:
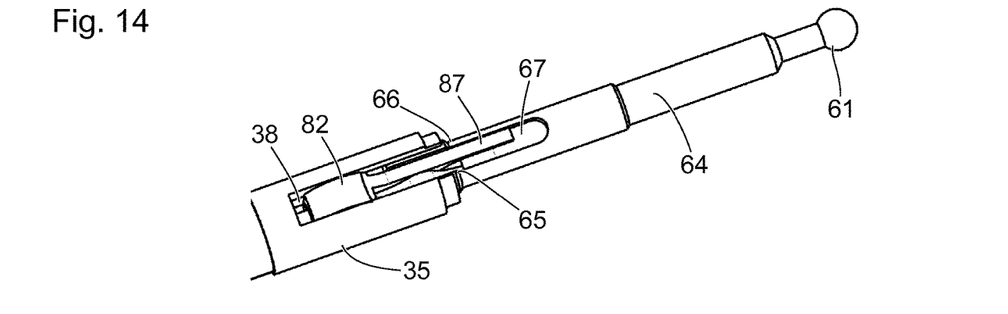
FIG. 14 shows another schematic view of the transmission adapter from FIG. 13.
Figure 15:
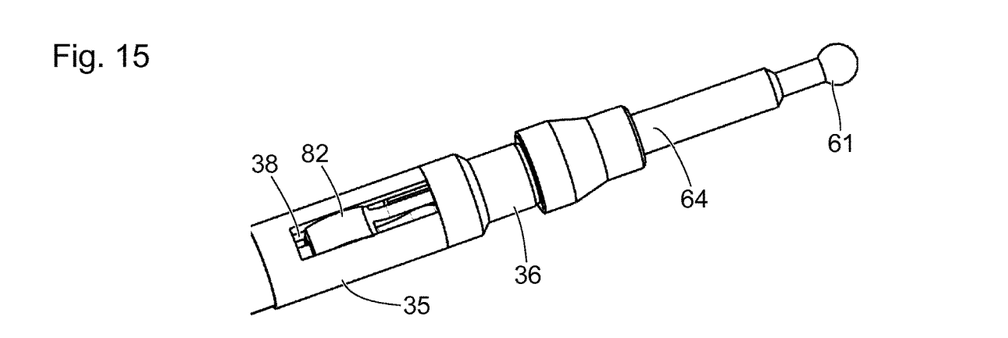
FIG. 15 shows another schematic view of the transmission adapter from FIGS. 13 and 14.

FIGS. 13 to 15 show schematic axonometric views of a transmission adapter 60 which, in terms of some features, corresponds to the transmission adapters described above with reference to FIGS. 5 to 10, particularly to the transmission adapter described above with reference to FIG. 9.

FIG. 13 shows only the transmission adapter 60 with a mechanically coupled transmission device 50. The main body 64 of the transmission adapter 60 has, at its proximal end, the spherical first coupling 61 and, at its distal end, two spars 65, 66 arranged in a fork shape. The grip jaws 81, 82 are connected to the spars 65, 66 by a shaft 89 parallel to their pivot axis 88 (cf. FIGS. 5 to 10). Each end of the shaft 89 is joined to a respective spar 65, 66. The mounting of the grip jaws 81, 82 on the shaft 89 permits the described pivoting function. The elastic elements 87 designed in one piece with the grip jaws 81, 82 bear against the abutment 67 on the main body 64.

In the view in FIG. 14, the distal end of the transmission adapter and in particular the grip jaws 81, 82 are arranged in a distal sleeve 35. In the view in FIG. 15, the distal sleeve 35 is supplemented by a proximal sleeve 36 for the proximal area of a shaft (or of a shaft adapter). The lateral openings 38, in which the grip jaws 82 are partially arranged, are formed by longitudinal slits in the distal sleeve 35.

In contrast to what is shown in FIGS. 2 to 12, the proximal area of the shaft formed by the sleeves 35, 36, in particular the proximal sleeve 36, has no circular cylindrical cross section. A broad and shallow annular groove allows a mechanical connection of the shaft to a manipulating device to be locked with a form fit, by means not shown in FIGS. 1 to 12.

In the illustrative embodiments described above with reference to FIGS. 2 to 15, the second coupling element 68 in each case comprises two grip jaws 81, 82, of which at least one is pivotable. Alternatively, the second coupling element 68 can comprise one or more grip jaws that are movable or displaceable along a predetermined straight or curved path. A grip jaw can be simultaneously pivotable and movable along a predetermined path. A path is predetermined, for example, by a slotted guide or a similar guide means that can couple a translation movement with a pivoting movement.

Figure 16:
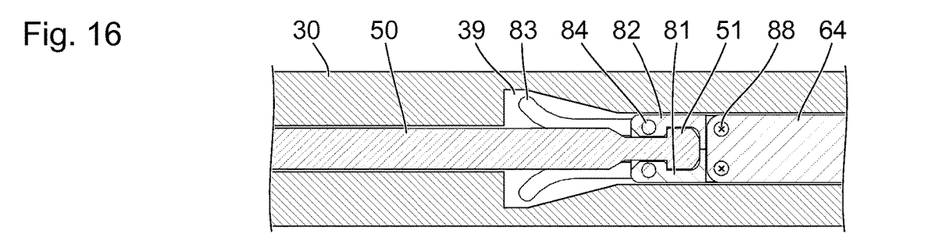
FIG. 16 shows a schematic view of another transmission adapter.

FIG. 16 shows a schematic view of a section through another transmission adapter. The sectional plane is parallel to the plane of the drawing in FIG. 1 and corresponds substantially to the sectional planes in FIGS. 2 to 12. Similarly as in FIGS. 5 to 12, only the distal end of the transmission adapter is shown. The proximal end of the transmission adapter corresponds, for example, to the proximal end described above with reference to FIGS. 2 to 4.

The second coupling element of the transmission adapter as shown in FIG. 16 comprises two grip jaws 81, 82. Each grip jaw is pivotable about a pivot axis 88 perpendicular to the sectional plane of FIG. 16. Each pivot axis 88 is defined by a pin or a bolt or a shaft, by means of which the grip jaw 81, 82 is connected in a hinged manner to a main body 64 of the transmission adapter.

The transmission adapter is arranged in a shaft 30, particularly in a proximal area of the shaft 30. The lumen of the shaft 30, in which a transmission device 50 is arranged, is widened to form a cavity, which also receives the transmission adapter. The distal end 39 of the cavity is designed to permit an outward pivoting of the grip jaws 81, 82 when the transmission adapter with the main body 64 and with the grip jaws 81, 82 is pushed in the distal direction relative to the position shown in FIG. 16.

Slotted guides 83 are arranged near the distal end 39 of the cavity. The slotted guides 83 each have a substantially straight proximal portion and a curved distal portion. On each grip jaw 81, 82, near the distal end thereof, a pin 84 is arranged which engages in one of the slotted guides 83. By means of the slotted guides 83 and the pins 84 engaging in the slotted guides 83, a linear movement of the transmission adapter between a proximal position shown in FIG. 16 and a distal position is coupled with a pivoting movement of the grip jaws 81, 82 about their pivot axes 88. In the proximal position of the transmission adapter as shown in FIG. 16, and in an area located distally from this position, the grip jaws 81, 82 are situated in the gripping or holding positions which are shown in FIG. 16 and in which they hold the proximal end 51 of the transmission device 50 with a form fit. In an area located farthest in the proximal direction, the grip jaws 81, 82 pivot away from each other and release the proximal end 51 of the transmission device 50.

Figure 17:
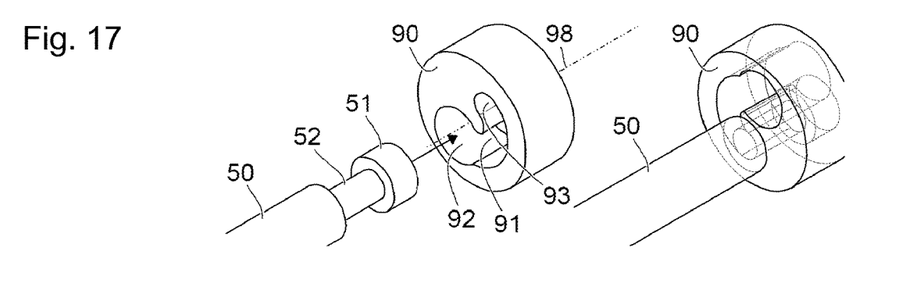
FIG. 17 shows schematic views of another transmission adapter.

FIG. 17 shows two schematic, axonometric views of another transmission adapter. In particular, a coupling member 90 of the transmission adapter is shown which can be coupled to a proximal end 51 of a transmission device. Further elements and components of the transmission adapter and a shaft or shaft adapter, in which the transmission adapter can be arranged, are not shown.

The coupling member 90 is rotatable about a rotation axis 98, which is substantially parallel to the longitudinal axis of a transmission device 50 to be coupled to the coupling member 90. The coupling member 90 has an opening or recess 91 with a first end 92 and a second end 93. The first end 92 has a cross section (with respect to a plane perpendicular to the rotation axis 98) which is adapted to the proximal end 51 of the transmission device 50. The proximal end 51 of the transmission device 50 can therefore be guided through the first end 92 of the recess 91, when the first end 92 of the recess 91 is aligned with the proximal end 51 of the transmission device 50, as is shown on the left in FIG. 17.

The second end 93 of the recess 91 has a cross section which is adapted to the cross section of a neck 52 located distally from the proximal end 51 of the transmission device 50. Therefore, the rotatable coupling member 90 can be rotated about its rotation axis 98 to the position shown on the right in FIG. 17, when the neck 52 of the transmission device lies in the recess 91. In the position of the rotatable coupling member 90 as shown on the right in FIG. 17, the transmission device 50 is coupled to the coupling member 90 with a form fit.

Figure 18:
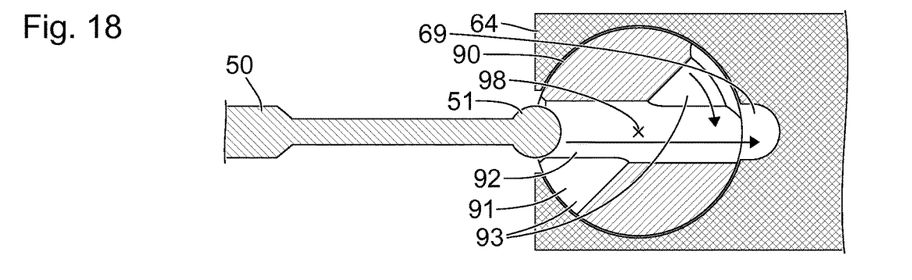
FIG. 18 shows a schematic view of another transmission adapter.
Figure 19:
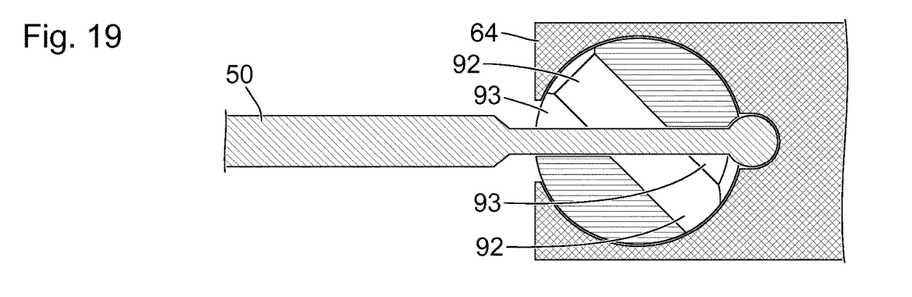
FIG. 19 shows another schematic view of the transmission adapter from FIG. 18.

FIGS. 18 and 19 show schematic sectional views of another transmission adapter. In particular, they show a distal end of the transmission adapter with a coupling element for coupling to a proximal end 51 of a transmission device 50. A proximal end (not shown in FIGS. 18 and 19) of the transmission adapter corresponds, for example, to the proximal end described above with reference to FIGS. 2 to 4. The sectional plane is parallel to the plane of the drawing in FIG. 1 and corresponds substantially to the sectional planes of FIGS. 2 to 12 and 16.

Within a main body 64, the transmission adapter comprises a coupling member 90 which is rotatable about a rotation axis 98 perpendicular to the sectional plane in FIGS. 18 and 19. The coupling member 90 is shown in two different positions in FIGS. 18 and 19. The coupling member 90 has a substantially circular cross section and is arranged in a corresponding cavity in the main body 64. The coupling member 90 has a recess 91, which passes all the way through the coupling member 90 from distal to proximal, parallel to the sectional plane of FIGS. 18 and 19.

The recess comprises a substantially circular cylindrical through-bore 92 which, at each end, has a keyhole-like widening 93 in a counterclockwise direction and parallel to the sectional plane of FIGS. 18 and 19. In terms of their mechanical interaction with the transmission device 50, or with the proximal end 51 of the latter, the circular cylindrical through-bore 92 corresponds to the first end, and the keyhole-like widenings 93 to the second end, of the recess in the rotatable coupling member of the illustrative embodiment in FIG. 17.

In the position of the coupling member 90 as shown in FIG. 18, the through-bore 92 is parallel to the longitudinal axis of the transmission device 50. As is indicated by a straight arrow, the proximal end 51 of the transmission device 50 can be guided all the way through the through-bore 92 to a niche 69 in the main body 64. Thereafter, as is indicated by a curved arrow, the coupling member 90 can be rotated about its rotation axis 98 as far as the position shown in FIG. 19. In the position of the coupling member 90 as shown in FIG. 19, the proximal end 51 of the transmission device is held in the niche 69 with a form fit by means of the coupling member 90.

Figure 20:
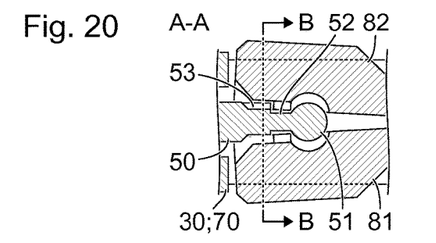
FIG. 20 shows a schematic view of part of another transmission adapter.

FIG. 20 shows a schematic and enlarged sectional view of part of another transmission adapter 60 (cf. FIGS. 2 to 4) which, in terms of some features, is similar to the transmission adapters described above with reference to FIGS. 2 to 15. The sectional plane of FIG. 20 corresponds to the sectional planes of FIGS. 2 to 12 and is parallel to the longitudinal axis 37 (cf. FIGS. 1 to 3) of the shaft. FIG. 20 shows a much smaller partial area of the transmission adapter than that shown in FIGS. 5 to 12. In particular, it shows only the area of the grip jaws 81, 82 of the second coupling element 68 of the transmission adapter 60 (cf. FIGS. 2 to 4).

The illustrative embodiment in FIG. 20 differs from the illustrative embodiments described above with reference to FIGS. 2 to 15 particularly in terms of a different design of the transmission device 50 and a corresponding design of the grip jaws 81, 82 of the second coupling element. In the area located distally, in particular immediately distally, from its spherical proximal end 51, the transmission device 50 has a short circular cylindrical neck 52 and, distally from this neck 52, a flattening 53. In the area of the flattening 53, the transmission device 50 has a substantially rectangular cross section with two substantially straight and flat sides lying opposite each other. The thickness or height of this substantially rectangular cross section corresponds, for example, to the diameter of the circular cylindrical neck 52. The width of the rectangular cross section of the flattening 53 in particular corresponds substantially to the diameter of the transmission device 50 distally from the flattening 53. In FIG. 20, the transmission device 50 is shown rotated about its longitudinal axis by an angle of ca. 45°.

Figure 21:
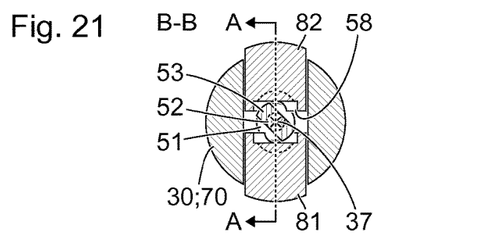
FIG. 21 shows another schematic view of the transmission adapter from FIG. 20.

FIG. 21 shows another schematic sectional view of the illustrative embodiment from FIG. 20. The sectional plane B-B of FIG. 21 is perpendicular to the sectional plane A-A of FIG. 20 and perpendicular to the longitudinal axis 37 (cf. FIG. 1). The position of the sectional plane B-B of FIG. 21 is indicated in FIG. 20. The position of the sectional plane A-A of FIG. 20 is indicated in FIG. 21.

It will be seen in FIG. 21 that the two grip jaws 81, 82 each have a recess 58 for receiving the flattening 53 on the transmission device 50. The substantially rectangular cross section of the flattening 53 can also be seen. In a departure from an ideal rectangle, the short sides of the cross section of the flattening 53 can be arc-shaped.

FIGS. 20, 21 show a configuration or situation in which the transmission device 50, in particular the flattening 53 on the transmission device 50, is rotated through ca. 45° in relation to a position predetermined by the shape of the flattening 53 and by the shape of the recess 58 in the grip jaws 81, 82. Starting from the configuration shown in FIGS. 20, 21, restoring forces generated by elastic elements 87 for example (cf. FIGS. 5 to 14), and acting on the grip jaws 81, 82, cause a rotation of the transmission device 50 to the predetermined position.

Figure 22:
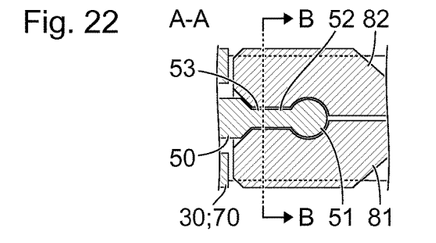
FIG. 22 shows another schematic view of the part of the transmission adapter from FIG. 20.

FIG. 22 shows another schematic sectional view of the illustrative embodiment from FIGS. 20, 21. The sectional plane A-A and the nature of the view in FIG. 22 correspond to those of FIG. 20. In FIG. 22, the transmission device 50 is shown in the above-described position predetermined by the shape of the flattening 53 and by the shape of the recesses 58 in the grip jaws 81, 82. The grip jaws 81, 82 adopt positions in which they bear on the proximal end 51, on the neck 52 and on the flattening 53 of the transmission device 50 and hold the transmission device 50 with a form fit in the predetermined position.

Figure 23:
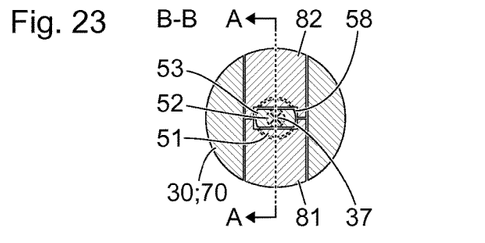
FIG. 23 shows another schematic view of the transmission adapter from FIGS. 20 to 21.

FIG. 23 shows another schematic sectional view of the illustrative embodiment from FIGS. 20 to 22. The sectional plane B-B of FIG. 23 corresponds to the sectional plane of FIG. 21. The situation or configuration shown in FIG. 23 corresponds to that of FIG. 22.

It will be seen from FIG. 23 that, in the situation or configuration shown in FIGS. 22, 23, a form fit between the grip jaws 81, 82 or the recesses 58 in the grip jaws 81, 82, on the one hand, and the flattening 53 on the transmission device 50, on the other hand, holds the transmission device 50 in the above-mentioned predetermined position in respect of a rotation about the longitudinal axis 37.

The holding of the transmission device 50 in the predetermined rotation position causes in particular a locking of a bayonet coupling or of a screw coupling or of another releasable mechanical connection of a tool 40 to the distal end 32 of a shaft 30 (cf. FIG. 1). Alternatively, the form-fit mechanical connection between the transmission adapter and the transmission device permits, for example, a rotation of the transmission device 50 about the longitudinal axis 37 by means of the transmission adapter, in order to rotate a tool 40 at the distal end 32 of a shaft 30.

Figure 24:
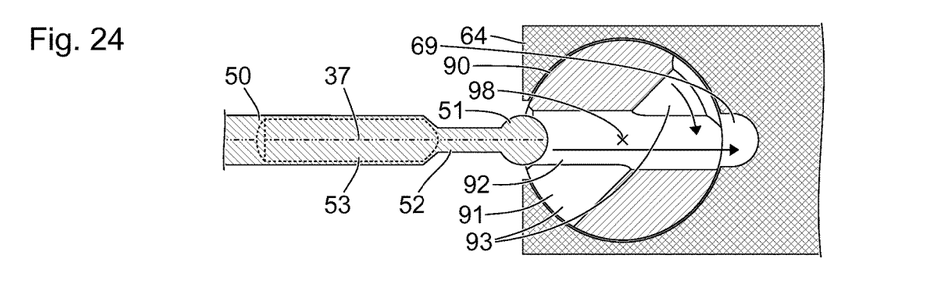
FIG. 24 shows a schematic view of another transmission adapter.

FIG. 24 shows a schematic sectional view of another transmission adapter and of a transmission device 50 which, in terms of some features and properties, are similar to those described above with reference to FIGS. 18 and 19. The sectional plane of FIG. 24 and the nature of the view also correspond to those of FIGS. 18 and 19. Only those features and properties are described below which differentiate the illustrative embodiment of FIG. 24 from the illustrative embodiment of FIGS. 18 and 19.

In the illustrative embodiment of FIG. 24, the transmission device 50 has a flattening 53 located distally from a substantially circular cylindrical neck 52. In the area of the flattening 53, the transmission device 50 has a substantially rectangular cross section with two flat sides lying opposite each other and substantially parallel to each other, similarly to the cross section of the flattening described above with reference to FIGS. 20 to 23. The rotatable coupling member 90 is substantially similar to the one described above with reference to FIGS. 18 and 19 and, in relation thereto, is adapted only to the cross section of the flattening 53.

Figure 25:
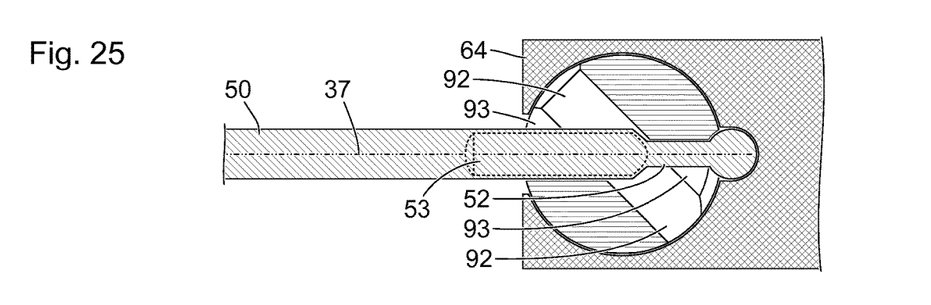
FIG. 25 shows another schematic view of the transmission adapter from FIG. 24.

FIG. 25 shows another schematic view of the illustrative embodiment from FIG. 24. The sectional plane and the nature of the view correspond to those of FIG. 24. The situation or configuration shown in FIG. 25 differs from the one shown in FIG. 24 in that, similarly to FIG. 19, the transmission device 50 is inserted completely into the transmission adapter and the rotatable coupling member 90 is rotated through ca. 45°. In the position of the coupling member 90 as shown in FIG. 25, the proximal end 51 of the transmission device 50 is held with a form fit in the niche 69 (cf. FIG. 24) by the coupling member 90. In this way, a mechanical connection, which is rigid in terms of forces and movements parallel to the longitudinal axis 37, is created between the coupling member 90 and the transmission device 50. Moreover, the flattening 53 on the transmission device 50 is held by the rotatable coupling member 90 such that the transmission device 50 cannot rotate about the longitudinal axis 37, and instead is also held in terms of rotation in the position shown in FIG. 25.

The holding of the transmission device 50 in the predetermined rotation position causes in particular a locking of a bayonet coupling or of a screw coupling or of another releasable mechanical connection of a tool 40 to the distal end 32 of a shaft 30 (cf. FIG. 1). Alternatively, the form-fit mechanical connection between the transmission adapter, comprising the coupling member 90, and the transmission device permits, for example, a rotation of the transmission device 50 about the longitudinal axis 37 by means of the transmission adapter, in order to rotate a tool 40 at the distal end 32 of a shaft 30.

Figure 26:
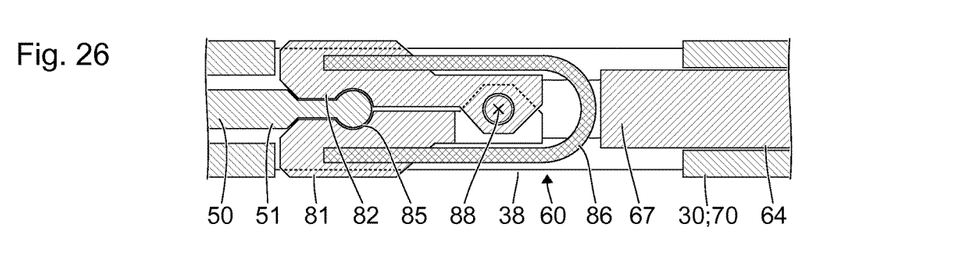
FIG. 26 shows a schematic view of another transmission adapter.

FIG. 26 shows a schematic view of another transmission adapter 60 which, in terms of some features, is similar to the transmission adapters described above with reference to FIGS. 2 to 12, in particular to the transmission adapter described above with reference to FIGS. 5 to 8. The nature of the view, in particular the sectional plane shown, corresponds to the views in FIGS. 5 to 12.

The transmission adapter 60 shown in FIG. 26 differs from the transmission adapter described above with reference to FIGS. 5 to 8 particularly in that an elastic element 86 is provided which is not designed in one piece with the grip jaws 81, 82. Instead, the elastic element 86 is provided as a component that is separately produced and that is then mechanically connected to the grip jaws 81, 82. In particular, the elastic element 86 is produced from a U-shaped piece of wire made of spring steel or of another elastic material, wherein the two ends of the elastic element 86 are fitted into corresponding bores in the grip jaws 81, 82.

Instead of a U-shaped elastic element 86, another kind of elastic element made from an elastic material can be provided which, during deflection of the grip jaws 81, 82 from their positions shown in FIG. 26, is exposed to stretching, compressing, twisting or shearing forces or moments and is elastically deformed. For example, the elastic element can be a leaf spring, or a helical spring stressed by tension or pressure. The elastic element can comprise a metal or a non-metallic material, for example an elastomer.

The elastic element 86 has the same function as the elastic elements 87 of the embodiments of FIGS. 5 to 15. In particular, the elastic element 86 applies forces or moments to the grip jaws, which move the latter in the direction of the positions shown in FIG. 26, in which they hold the proximal end 51 of a transmission device 50 with a form fit.

Figure 27:
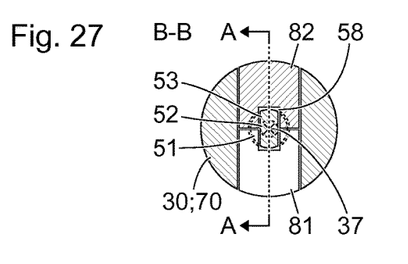
FIG. 27 shows a schematic view of part of another transmission adapter.

FIG. 27 shows a schematic and enlarged sectional view of part of another transmission adapter 60 (cf. FIGS. 2 to 4) which, in terms of some features, is similar to the transmission adapters described above with reference to FIGS. 2 to 15. The sectional plane B-B of FIG. 27 is perpendicular to the longitudinal axis 37 (cf. FIG. 1) and corresponds to the sectional planes of FIGS. 21 and 23.

The embodiment of FIG. 27 differs from the embodiment of FIGS. 20 to 23 particularly in terms of other cross sections of the flattening 53 on the transmission device in the intended position, and corresponding cross sections of the recesses 58 on the grip jaws 81, 82. The cross section of the flattening 53 on the transmission device 50, in the position defined by the recesses 58 on the grip jaws and shown in FIG. 27, is turned through 90 degrees relative to the embodiment of FIGS. 20 to 23. Accordingly, the recesses 58 are not shallow and broad, but narrow and deep.

The design of the flattening 53 and of the recesses 58 on the grip jaws 81, 82 according to FIG. 27 can allow the transmission device 50 to be held in the depicted rotation position even when the grip jaws 81, 82 are not held, by an elastic element or elastic elements or by a form fit, in their position in which they hold the proximal end 51 of a transmission device 50 with a form fit.

LIST OF REFERENCE SIGNS 10 medical instrument
20 manipulating device
21 first part of the manipulating device 20
22 second part of the manipulating device 20
23 wheel on the manipulating device 20
25 recess
26 recess in the second part 22
28 pivot axis of the second part 22
30 shaft
31 proximal end of the shaft 30
32 distal end of the shaft 30
35 distal sleeve
36 proximal sleeve
37 longitudinal axis of the shaft 30
38 lateral opening at the proximal end 31 of the shaft 30 or of the shaft adapter 70
39 distal end of a cavity
40 tool
41 proximal end of the tool 40
42 distal end of the tool 40
43 stationary jaw part of the tool 40
44 pivotable jaw part of the tool 40
50 transmission device
51 proximal end of the transmission device 50
52 neck located distally from the proximal end 51 of the transmission device 50
53 flattening located distally from the neck 52
58 recess on grip jaw 81
60 transmission adapter
61 first coupling element of the transmission adapter 60
64 main body of the transmission adapter 60
65 first spar
66 second spar
67 abutment for elastic portions 87 of the grip jaws 81, 82
68 second coupling element of the transmission adapter 60
69 niche in the main body 64
70 shaft adapter
71 proximal end of the shaft adapter 70
72 distal end of the shaft adapter 70
73 recess at the distal end 72 of the shaft adapter 70
81 first grip jaw of the second coupling element 68
82 second grip jaw of the second coupling element 68
83 slotted guide
84 pin
85 concave portion on the first grip jaw 81
86 elastic element
87 elastic element
88 pivot axis of the grip jaws 81, 82
89 shaft
90 rotatable coupling member
91 recess in the rotatable coupling member 90
92 first end of the recess 91
93 second end of the recess 91
98 rotation axis of the rotatable coupling member 90

The invention claimed is:

1. A system including a transmission adapter for a medical instrument, the system comprising:
   a shaft;
   a transmission device movable in the shaft;
   a manipulating device with a first part rigidly coupled to a proximal end of the shaft such that the first part and the proximal end of the shaft are positionally fixed relative to one another during use of the medical instrument, and a second part movable relative to the first part;
   a first coupling element configured to be releasably coupled to the second part of the manipulating device; and
   a second coupling element configured to be releasably coupled to a proximal end of the transmission device, and configured to transmit a torque to the transmission device when coupled to the transmission device;
   wherein the second coupling element comprises a movable grip jaw configured to hold the proximal end of the transmission device with a form fit or force fit, and an elastic element configured to mechanically pretension the movable grip jaw to a position gripping the proximal end of the transmission device; and
   wherein the movable grip jaw is configured to lie completely within a contour of the shaft when the proximal end of the transmission device is held with the form fit or force fit by the movable grip jaw, and to protrude beyond the contour of the shaft when the movable grip jaw is uncoupled from the proximal end of the transmission device.

2. The system according to claim 1, the second coupling element is configured to be locked when the second coupling element is arranged in the manipulating device.

3. The system according to claim 1, wherein the first coupling element has a surface portion in the shape of a spherical surface.

* * * * *